US008718786B2

(12) United States Patent
Shalev

(10) Patent No.: US 8,718,786 B2
(45) Date of Patent: *May 6, 2014

(54) ELECTRICAL STIMULATION IN THE MIDDLE EAR FOR TREATMENT OF HEARING RELATED DISORDERS

(75) Inventor: Alon Shalev, Raanana (IL)

(73) Assignee: Estimme Ltd., Tel Aviv (IL)

(*) Notice: Subject to any disclaimer, the term of this patent is extended or adjusted under 35 U.S.C. 154(b) by 697 days.

This patent is subject to a terminal disclaimer.

(21) Appl. No.: 12/678,301

(22) PCT Filed: Aug. 31, 2008

(86) PCT No.: PCT/IL2008/001178
§ 371 (c)(1),
(2), (4) Date: Sep. 7, 2010

(87) PCT Pub. No.: WO2009/037689
PCT Pub. Date: Mar. 26, 2009

(65) Prior Publication Data
US 2010/0198302 A1    Aug. 5, 2010

Related U.S. Application Data

(60) Provisional application No. 60/973,772, filed on Sep. 20, 2007, provisional application No. 61/026,245, filed on Feb. 5, 2008.

(51) Int. Cl.
*A61N 1/05*    (2006.01)
(52) U.S. Cl.
USPC ............... 607/57; 607/56; 607/115; 607/137
(58) Field of Classification Search
USPC ............... 607/2, 55–57, 136, 137, 115, 116; 623/10
See application file for complete search history.

(56) References Cited

U.S. PATENT DOCUMENTS

| 4,762,135 | A | * | 8/1988 | van der Puije et al. ....... 607/116 |
| 5,545,219 | A | * | 8/1996 | Kuzma ............................ 623/10 |
| 5,788,656 | A | | 8/1998 | Mino |
| 5,922,016 | A | | 7/1999 | Wagner |
| 6,157,861 | A | | 12/2000 | Faltys et al. |
| 6,210,321 | B1 | | 4/2001 | Di Mino et al. |
| 6,295,472 | B1 | | 9/2001 | Rubinstein |
| 6,456,886 | B1 | | 9/2002 | Howard, III et al. |
| 6,631,295 | B2 | | 10/2003 | Rubinstein et al. |
| 2001/0053872 | A1 | | 12/2001 | Zilberman et al. |
| 2002/0019668 | A1 | | 2/2002 | Stockert et al. |

(Continued)

OTHER PUBLICATIONS

International Search Report for corresponding PCT application (PCT/IL2008/001178), 2 pages, mailed Feb. 3, 2009.
Extended European search report for nationalized EPO application of the corresponding PCT application (PCT/IL2008/001178), 5 pages, mailed Dec. 29, 2010.
PCT written opinion of the ISA for the corresponding PCT application (PCT/IL2008/001178), 9 pages, mailed Feb. 3, 2009.

*Primary Examiner* — Eric D. Bertram
*Assistant Examiner* — Pamela M Bays
(74) *Attorney, Agent, or Firm* — Roach Brown McCarthy & Gruber, P.C.; Kevin D. McCarthy

(57) ABSTRACT

An auditory implant system for treating a hearing disorder is disclosed. Methods are also disclosed for the use thereof. The system comprises an implantable array of electrodes and a pulse generator (PG), wherein at least one electrode is a cochlear effecting electrode adapted for disposition in the associated Eustachian tube in the proximity of the associated fenestra rotunda.

14 Claims, 12 Drawing Sheets

(56) References Cited

U.S. PATENT DOCUMENTS

| | | |
|---|---|---|
| 2002/0029070 A1 | 3/2002 | Leysieffer et al. |
| 2002/0051550 A1 | 5/2002 | Leysieffer |
| 2002/0099421 A1 | 7/2002 | Goldsmith et al. |
| 2004/0230254 A1* | 11/2004 | Harrison et al. ............... 607/57 |
| 2004/0236390 A1 | 11/2004 | Dadd et al. |
| 2005/0240147 A1* | 10/2005 | Makower et al. .......... 604/96.01 |
| 2006/0095066 A1 | 5/2006 | Chang et al. |
| 2007/0005117 A1 | 1/2007 | Fritsch et al. |
| 2007/0055308 A1* | 3/2007 | Haller et al. ...................... 607/2 |

* cited by examiner

ELECTRICAL STIMULATION IN THE MIDDLE EAR FOR TREATMENT OF HEARING RELATED DISORDERS

REFERENCE TO CO-PENDING APPLICATIONS

Priority is claimed from a 371 of international of PCT/IL2008/001178, filed on Aug. 31, 2008, which claims priority to U.S. provisional patent application Nos. 60/973,772, filed on Sep. 20, 2007; and 61/026,245, filed on Feb. 5, 2008.

FIELD OF THE INVENTION

This invention relates generally to a system and method for treatment of hearing disorders and more particularly to a system which includes a middle ear effecting electrode for applying electrical signals in waveform to the cochlea.

BACKGROUND OF THE INVENTION

There are a number of hearing disorders which cause a great deal of suffering to mankind and various attempts have been made to relieve them.
Tinnitus Tinnitus is the perception of sound in the human ear in the absence of corresponding external sound(s). Tinnitus can be perceived in one or both ears or in the head. It is usually described as a ringing noise, but in some patients it takes the form of a high pitched whining, buzzing, hissing, humming, or whistling sound, or as ticking, clicking, roaring, "crickets" or "tree frogs" or "locusts", tunes, songs, or beeping. It has also been described as a "whooshing" sound, as of wind or waves. Tinnitus is not itself a disease but a symptom resulting from a range of underlying causes, including ear infections, foreign objects or wax in the ear, and injury from loud noises. Tinnitus is also a side-effect of some oral medications, such as aspirin, and may also result from an abnormally low level of serotonin activity.

The sound perceived may range from a quiet background noise to one that can be heard even over loud external sounds. The term "tinnitus" usually refers to more severe cases. Heller and Bergman (1953) conducted a study of 80 tinnitus-free university students placed in an anechoic chamber and found that 93% reported hearing a buzzing, pulsing or whistling sound. Cohort studies have demonstrated that damage to hearing from unnatural levels of noise exposure is very widespread in industrialized countries.

Because tinnitus is often defined as a subjective phenomenon, it is difficult to measure using objective tests, such as by comparison to noise of known frequency and intensity, as in an audiometric test. The condition is often rated clinically on a simple scale from "slight" to "catastrophic" according to the practical difficulties it imposes, such as interference with sleep, quiet activities, or normal daily activities. For research purposes, the more elaborate Tinnitus Handicap Inventory is often used. In a minority of cases, a clinician can perceive an actual sound (e.g., a bruit) emanating from the patient's ears. This is called objective tinnitus. Objective tinnitus can arise from muscle spasms that cause clicks or crackling around the middle ear. Some people experience a sound that beats in time with the pulse (i.e. pulsatile tinnitus). Pulsatile tinnitus is usually objective in nature, resulting from altered blood flow or increased blood turbulence near the ear (such as from atherosclerosis or venous hum, but it can also arise as a subjective phenomenon from an increased awareness of blood flow in the ear. Rarely, pulsatile tinnitus may be a symptom of potentially life-threatening conditions such as carotid artery aneurysm or carotid artery dissection. The basis of quantitative measurement of tinnitus relies on the brain's tendency to select out only the loudest sounds heard. Based on this tendency, the amplitude of a patient's tinnitus can be measured by playing sample sounds of known amplitude and asking the patient which he or she hears. The tinnitus will always be equal to or less than sample noises heard by the patient. This method works very well to gauge objective tinnitus (see above.) For example: if a patient has a pulsatile paraganglioma in his ear, he will not be able to hear the blood flow through the tumor when the sample noise is 5 decibels louder than the noise produced by the blood. As sound amplitude is gradually decreased, the tinnitus will become audible, and the level at which it does so provides an estimate of the amplitude of the objective tinnitus.

Objective tinnitus, however, is quite uncommon. Often patients with pulsatile tumors will report other coexistent sounds, distinct from the pulsatile noise, that will persist even after their tumor has been removed. This is generally subjective tinnitus, which, unlike the objective form, cannot be tested by comparative methods. If a subject is focused on a sample noise, they can often detect it to levels below 5 decibels, which would indicate that their tinnitus would be almost impossible to hear. Conversely, if the same test subject is told to focus only on their tinnitus, they will report hearing the sound even when test noises exceed 70 decibels, making the tinnitus louder than a ringing phone. This quantification method suggests that subjective tinnitus relates only to what the patient is attempting to hear. Patients actively complaining about tinnitus could thus be assumed to be people who have become obsessed with the noise. This is only partially true. The problem is involuntary; generally complaining patients simply cannot override or ignore their tinnitus. The noise is often present in both quiet and noisy environments, and can become quite intrusive to their daily lives. Subjective tinnitus may not always be correlated with ear malfunction or hearing loss. Even people with near-perfect hearing may still complain of it. Tinnitus may also have a connection to memory problems, anxiety, fatigue or a general state of poor health.

One of the possible mechanisms relies in the otoacoustic emissions. The inner ear contains thousands of minute hairs which vibrate in response to sound waves and cells which convert neural signals back into acoustical vibrations. The sensing cells are connected with the vibratory cells through a neural feedback loop, whose gain is regulated by the brain. This loop is normally adjusted just below onset of self-oscillation, which gains the ear spectacular sensitivity and selectivity. If something changes, it's easy for the delicate adjustment to cross the barrier of oscillation and tinnitus results. This can actually be measured by a very sensitive microphone outside the ear.

Other possible mechanisms of how things can change in the ear is damage to the receptor cells. Although receptor cells can be regenerated from the adjacent supporting Deiters cells after injury in birds, reptiles, and amphibians, in mammals it is believed that they can be produced only during embryogenesis. Although mammalian Deiters cells reproduce and position themselves appropriately for regeneration, they have not been observed to trans-differentiate into receptor cells except in tissue culture experiments. Therefore, if these hairs become damaged, through prolonged exposure to excessive decibel levels, for instance, then deafness to certain frequencies occurs. In tinnitus, they may falsely relay information at a certain frequency that an externally audible sound is present, when it is not.

The mechanisms of subjective tinnitus are often obscure. While it is not surprising that direct trauma to the inner ear can cause tinnitus, other apparent causes (e.g., temporomandibular joint disorder, (TMJ) and dental disorders) are difficult to explain. Recent research has proposed that there are two distinct categories of subjective tinnitus: otic tinnitus, caused by disorders of the inner ear or the acoustic nerve, and somatic tinnitus, caused by disorders outside the ear and nerve but still within the head or neck. It is further hypothesized that somatic tinnitus may be due to "central crosstalk" within the brain, as certain head and neck nerves enter the brain near regions known to be involved in hearing.

While most discussions of tinnitus tend to stress physical mechanisms, there is strong evidence that the level of an individual's awareness of their tinnitus can be stress-related, and so should be addressed by improving the state of the nervous system generally, using gradual, unobtrusive, long-term treatments.

While there are a few effective treatments for objective tinnitus, there is no methodoligical array of solutions for subjective tinnitus.

Tinnitus can have many different causes, but most commonly results from otologic disorders—the same conditions that cause hearing loss. The most common cause is noise-induced hearing loss, resulting from exposure to excessive or loud noises. Ototoxic drugs can cause tinnitus either secondary to hearing loss or without hearing loss, and may increase the damage done by exposure to loud noise, even at doses that are not in themselves ototoxic.

Howard, III, et al. in U.S. Pat, Nos. 6,456,886 and 5,697,975 describe a neural prosthetic device for reducing or eliminating the effects of tinnitus that includes a stimulation device and an electrode arranged in the primary auditory cortex. Mino in U.S. Pat. No. 5,788,656 describes an electronic stimulation system for treating tinnitus. It includes a probe that is placed at a site in proximity to the cochlea of the inner ear whereby the probe vibrations are transmitted to the cochlea. Wagner in U.S. Pat. No. 5,922,016 describes an apparatus for electric stimulation and diagnostics of auditory nerves of a human being that includes a stimulator detachably secured to a human being for sending a signal into a human ear, and an electrode placed within the human ear and electrically connected to the stimulator by an electric conductor for conducting the signals from the stimulator into the ear. A control unit is operatively connected to the stimulator for instructing the stimulator as to characteristics of the generated signals being transmitted to the ear. The electrodes that are placed within the auditory meatus are formed by a body of electrically conducting material such as e.g. graphite, metal or the like, and connected via an electric conductor to the stimulator, whereby the conductor is secured in place by an enveloping plastic body of elastically deformable material which bears upon the inside wall of the auditory meatus and which may also be used for sealing the auditory meatus. When being placed in the middle ear, preferably upon the promontory, Wagner describes the electrode in form of a body of electrically conducting material such as graphite, metal or the like, which is situated at the end of an insulated metal rod with electrical conduction. The metal rod is formed preferably in crank-like manner and is secured in place by an enveloping plastic body of elastically deformable material that bears upon the inner wall of the auditory meatus. Such a placement is claimed to be particularly effective to stimulate the auditory nerves.

Faltys et al. in U.S. Pat. No. 6,157,861 describe self-adjusting cochlear implant system and method which uses an implanted middle ear electrode to determine the middle ear reflex response. Rubinstein in U.S. Pat. No. 6,295,472 describes a method for generating pseudospontaneous activity in an auditory nerve and a system for treatment of tinnitus, comprising an adaptor that modifies a pseudospontaneous signal and an electrical contact adapted to be affixed nearby the cochlea.

Rubinstein et al. in U.S. Pat. No. 6,631,295 describe a method of diagnosing whether a human is a candidate for tinnitus reduction using a neural prosthetic. Di Mina et al. in U.S. Pat. No. 6,210,321 describe an electronic stimulation system for treating tinnitus. The system includes an electrodynamically-actuated diaphragm and probe assembly acting as an applicator to cause the probe to vibrate. The probe is placed at a site in proximity to the cochlea.

Zilberman et al. in U.S. Pat. App. No. 20010053872 describe a hearing aid comprised of conventional cochlear implant electronics implanted in the middle ear and coupled to an actuator configured to mechanically vibrate the middle ear ossicles. Stockert et al, in U.S. Pat. App. No. 20020019668 describe a hearing system for rehabilation of a hearing disorder, comprising an output member for stimulating, via a passive coupling element, an ossicle of a middle ear.

Leysieffer et al. in U.S. Pat. App. No. 20020029070 describe an implantable system for rehabilitation of a hearing disorder with output-side electromechanical transducers for stimulation of the fluid-filled inner ear spaces. Leysieffer in U.S. Pat. App. No. 20020051550 describes hermetically sealed housing for an implantable medical device with separation wall which divides the housing to two chambers.

Goldsmith et al. in U.S. Pat. App. No. 20020099421 describe a transcanal, transtympanic cochlear implant system comprising a first component for removable positioning within the auditory canal, and a second component for implantation within the middle ear space, comprising an insulated receiver coil disposed between second and third bones, and a wire mesh electrode located within the receiving coil functioning as a ground electrode.

Based on the abovementioned prior art, it is evident that the middle ear has been previously conceived as a possible site for coupling mechanical vibrations to the (bony) conductive chain of the ear. This type of stimulation would probably be more suitable for hearing disorders that are classically categorized as conductive.

Meniere's Disease

Also called idiopathic endolymphatic hydrops, it is a disorder of the inner ear. Although the cause is unknown, it probably results from an abnormality in the fluids of the inner ear. Meniere's disease is one of the most common causes of dizziness originating in the inner ear. In most cases only one ear is involved, but both ears may be affected in about 15% of patients. Meniere's disease typically starts between the ages of 20 and 50 years. Men and women are affected in equal numbers. Usually, in case vertigo attacks are not controlled by conservative measures and are disabling, one of the following surgical procedures might be recommended:

a. The endolymphatic shunt or decompression procedure is an ear operation that is usually preserves hearing. Attacks of vertigo are controlled in one-half to two-thirds of cases, but control is not permanent in all cases. Recovery time after this procedure is short compared to the other procedures.

b. Selective vestibular neurectomy is a procedure in which the balance nerve is cut as it leaves the inner ear and goes to the brain. Vertigo attacks are permanently cured in a high percentage of cases, and hearing is preserved in most cases.

c. Labyrinthectomy and eighth nerve section are procedures in which the balance and hearing mechanism in the inner ear are destroyed on one side. This is considered when the patient with Meniere's disease has poor hearing in the affected ear. Labyrinthectomy and eighth nerve section result in the highest rates for control of vertigo attacks.

Dizziness

A vague term describing various sensations, including a subjective feeling of uncertainty, postural instability, or motion in space. It also encompasses other sensations (e.g. light-headedness, wooziness, near fainting). The elderly often use the term even more broadly to include weakness, fatigue, and myriad other symptoms. Dizziness can be classified, somewhat arbitrarily, as acute (present for <1 month) or chronic (present for >1 month). Because the causes, diagnosis, and treatment of acute dizziness are similar for all adults, this chapter discusses only chronic dizziness and postural instability. The prevalence of chronic dizziness among the elderly ranges from 13 to 30%.

Dizziness is divided by history of sensation into five categories: (1) vertigo: a rotary motion, either of the patient with respect to the environment (subjective vertigo) or of the environment with respect to the patient (objective vertigo), the key element being the perception of motion; (2) disequilibrium (unsteadiness, imbalance, gait disturbance): a feeling (primarily involving the trunk and lower extremities rather than the head) that a fall is imminent; (3) presyncope (faintness, lightheadedness): a feeling that loss of consciousness is imminent; (4) mixed dizziness: a combination of two or more of the above types; and (5) nonspecific dizziness: a sensation of instability that does not fit readily into any of the previous categories.

Otosclerosis

As sound impinges upon the eardrum, it vibrates, causing the ossicles to move. The sound is then transmitted through to the inner ear. The chain of ossicles must be able to move freely for you to have normal hearing. The last bone in the chain is called the stapes. Otosclerosis causes new bone to grow over the stapes. This leads to a reduction in movement and eventually the bone becomes fixed. This reduces the transfer of sound to your inner ear and causes hearing loss. In the early stages of otosclerosis, or when the condition is mild, a patient might not need any treatment. However, sodium fluoride tablets have been shown to help prevent the progression of otosclerosis, but only if the condition has affected the inner ear.

Hearing aids can be very helpful and will typically be recommended before any surgical intervention is considered. However, otosclerosis typically continues to progress and hearing aids will not stop you developing profound deafness in the long term.

The common surgical treatment for otosclerosis is called stapedectomy. This operation aims to improve hearing by replacing the stapes—one of the ossicles—with a piston. The piston helps to restore the movement of the ossicles, so transmitting sound into the inner ear. Most of the stapes bone is removed, leaving just the portion called the footplate, which sits in contact with the oval window. The oval window is the link between the middle and inner ear. A small hole is then drilled in the footplate and the piston is inserted so that it sits in contact with the oval window. At its other end, the piston is attached to the incus, the middle of the three ossicles. However surgery may not relieve the tinnitus, and in case the inner ear is also affected, surgery may not improve the hearing either.

Hearing Loss

Hearing loss occurs when there is loss of sound sensitivity produced by an abnormality anywhere in the auditory system. A wide variety of conditions can cause hearing loss, including otosclerosis, cholesteatoma, and others. While physicians can sometimes identify the causes of hearing loss, in some cases the causes are unknown, or idiopathic.

Conductive Hearing Loss

Conductive hearing loss occurs when sound waves are prevented from passing from the air to the fluid-filled inner ear. This may be caused by a variety of problems including buildup of earwax (cerumen), infection, fluid in the middle ear, a punctured eardrum, or fixation of the ossicles, as in otosclerosis. Other causes include scarring, narrowing of the ear canal, tumors in the middle ear, and perforation of the tympanic membrane. Once the cause is found and removed or treated, hearing is usually restored.

Sensorineural Hearing Loss

Sensorineural hearing loss develops when the auditory nerve or hair cells in the inner ear are damaged. The source may be located in the inner ear, the nerve from the inner ear to the brain, or in the brain. Sensorineural hearing loss, commonly referred to as "nerve deafness," frequently occurs as a result of the aging process in the form of presbycusis, which is a gradual loss occurring in both ears. Tumors such as acoustic neuromas can lead to sensorineural hearing losses, as can viral infections, Meniere's disease, meningitis, and cochlear otosclerosis. Sensorineural hearing loss can also be the result of repeated, continuous loud noise exposure, certain toxic medications, or an inherited condition. Generally, it is non-reversible. Scientists have, however, made great progress in uncovering the genes responsible for a number of forms of congenital hearing impairments/deafness, and this genetic research may in time lead to therapies for some congenital causes of hearing loss. Sensorineural hearing loss may be further differentiated as sensory or neural. Sensory hearing loss refers to loss caused by abnormalities in the cochlea, such as by damage from noise trauma, viral infection, drug toxicity, or Meniere's disease. Neural loss stems from problems in the auditory (eighth cranial) nerve, such as tumors or neurologic disorders. While tumors in this nerve may be life threatening, they are also often curable.

Mixed Hearing Loss

A combination of both conductive and sensorineural hearing loss. Hearing loss may be partial or total. It may develop gradually or suddenly. People with hearing loss may experience difficulties hearing conversations, especially if there is background noise. Hissing, roaring, or ringing in the ears (tinnitus) occurs in some conditions, as may dizziness or problems with balance (vertigo). On the other hand, there is also plentiful prior art that teaches embodiments of direct electrical stimulation of the cochlea. These applications usually aim to address hearing disorders of a more sensoryneural nature A main down side to direct electrical stimuli of the cochlea is the relatively high invasiveness of the implantation procedure and the acute and longer-term risks that are related to having gone through such a procedure and having such a device in place. The underlining concept of currently commercially available cochlear implants is based on an electrode array implanted along the curls of the cochlea and stimulating the different areas of the cochlea that span the desired frequency spectrum. Therefore, a non specific current being directed from the middle ear at the cochlea without discrimination of its different regions will not be effective in contemporary hearing aids that are based on separate stimulation per frequency bands.

Direct electrical stimuli of the cochlea could be considered as a method for relieving tinnitus. A main down side to direct electrical stimuli of the cochlea is the relatively high invasiveness of the implantation procedure and the acute and longer-term risks that are related to having gone through such a procedure and having such a device in place.

The Eustachian tube (or auditory tube) is a tube that links the pharynx to the middle ear. In adults the Eustachian tube is approximately 35 mm long. Some modern medical books call this the pharyngotympanic tube. The Eustachian tube extends from the anterior wall of the middle ear to the lateral wall of the nasopharynx, approximately at the level of the inferior nasal concha. A portion of the tube (~⅓) proximal to the middle ear is made of bone; the rest is composed of cartilage and raises a tubal elevation, the torus tubarius, in the nasopharynx where it opens. The Eustachian tube evidently represents a much less invasive implantation route, compared to contemporary methods for placing cochlear electrodes directly in the middle ear—risking infection and possibly irreversibly damage to sensitive sensory and other neural structures.

It is a long felt and unmet need therefore to provide an auditory implant system for treating a hearing disorder which is minimally invasive. Furthermore, such an implant system which provides electrical signals to the cochlea and is implanted via the Eustachian tubes would answer an unmet and long felt need.

SUMMARY

An aspect of the invention is to provide an auditory implant system for treating a hearing disorder. The system comprises an implantable array of electrodes and a pulse generator (PG), wherein at least one electrode is a cochlear effecting electrode (CEE) adapted for affecting the cochlea of one first ear of a patient The CEE is further adapted for disposition in the associated first Eustachian tube in the proximity of the associated first fenestra rotunda.

A further aspect of the invention is to provide the aforementioned system wherein the array further comprises at least one return electrode and further wherein the pulse generator (PG) is adapted for generating an effecting electrical signal, to the cochlea via the effecting electrode.

A further aspect of the invention is to provide the aforementioned system further comprising a support structure, in which at least a portion of the array is mounted or is formed therefrom.

A further aspect of the invention is to provide the aforementioned system further comprising a support structure, in which at least one CEE is mounted or is formed therefrom. A further aspect of the invention is to provide the aforementioned system wherein the electrode array further comprises at least one second effecting electrode (SEE) adapted for effecting the associated cochlea of one second ear of a patient, the SEE further adapted for disposition in the associated second Eustachian tube in the proximity of the associated second fenestra rotunda and further wherein the pulse generator is adapted to deliver an electrical signal to the second cochlea via the SEE.

A further aspect of the invention is to provide the aforementioned system according to wherein the system additionally comprises the support structure adapted for
a. conveying the electrodes from at least a portion of the Eustachian tube to the proximity of the fenestra rotunda and
b. anchoring the electrodes from the proximity of the fenestra rotunda to a portion of the Eustachian tube.

A further aspect of the invention is to provide the aforementioned system wherein the support structure is adapted for transitioning between
a. a first radially collapsed conveying configuration and
b. a second radially expanded anchoring configuration, the configurations respectively facilitating the conveyance of the support structure through the portion of Eustachian tube and anchoring of the support structure at the portion of Eustachian tube, thereby disposing at least a portion of the array in proximity of the associated first fenestra rotunda.

A further aspect of the invention is to provide the aforementioned system wherein an anchoring means is attached to or formed from the support structure.

A further aspect of the invention is to provide the aforementioned system wherein a conveying means projects from, or is formed from the support structure.

A further aspect of the invention is to provide the aforementioned system wherein the support structure comprises a generally tubular engagement portion adapted to fit longitudinally in the Eustachian tube, the tubular engagement portion further comprising a proximal end, a distal end and a body connecting therebetween; wherein at least one the effecting electrode is disposed near the distal end of the engagement portion, further wherein the distal end of engagement portion is adapted to internally engage a portion of the Eustachian tube such that the distal conductive tip portion of the effecting electrodes is anchored in position when disposed in the proximity to the fenestra.

A further aspect of the invention is to provide the aforementioned system wherein the system additionally comprises a delivery apparatus for releasably deploying the support structure within the Eustachian tube thereby actuating transitioning of the engagement portion from the first radially collapsed configuration to the second radially expanded configuration, A further aspect of the invention is to provide the aforementioned system wherein the delivery apparatus comprises an endoscopic visualization channel.

A further aspect of the invention is to provide the aforementioned system wherein the endoscopic visualization channel has an external diameter between about 400 micrometers to about 1000 micrometers.

A further aspect of the invention is to provide the aforementioned system of claim the support structure is adapted for endoluminal retrieval following the transition from the radially expanded configuration to the radially collapsed configuration.

A further aspect of the invention is to provide the aforementioned system wherein the support structure is provided with a plurality of proximally disposed retrieval handles, the handles adapted to engage with and actuate a retrieval apparatus, the retrieval apparatus provided with means of transitioning the support structure from the radially expanded configuration to radially collapsed configuration and subsequent disposition into a tubular sheath.

A further aspect of the invention is to provide the aforementioned system wherein the engagement portion comprises a self expanding stent-like structure.

A further aspect of the invention is to provide the aforementioned system wherein the engagement portion comprises an open weave construction of helically wound filaments of a superelastic alloy.

A further aspect of the invention is to provide the aforementioned system wherein the length of the generally tubular engagement portion is between about 4 millimeters to about 14 millimeters.

A further aspect of the invention is to provide the aforementioned system wherein the cross section of the engagement portion is between about 4 millimeters to about 14 millimeters.

A further aspect of the invention is to provide the aforementioned system wherein the cross section of the engagement portion is conic, expanding from the proximal end towards the distal end of the tubular engagement portion.

A further aspect of the invention is to provide the aforementioned system wherein the distal end of the engagement portion is characterized by an oval cross section of about 2 millimeters×about 5 millimeters.

A further aspect of the invention is to provide the aforementioned system wherein the system further comprises the support structure provided with an extension arm, the extension arm adapted for post implant adjustment by the physician with or without a special tool for the purpose.

A further aspect of the invention is to provide the aforementioned system wherein the system further comprises a pulse generator provided with coupling means to any of the electrodes.

A further aspect of the invention is to provide the aforementioned system wherein the coupling means is selected from a group consisting of a radio frequency link, an acoustic energy link, a magnetic induction link or an electric lead.

A further aspect of the invention is to provide the aforementioned system wherein the support structure is a return electrode A further aspect of the invention is to provide the aforementioned system wherein the CEE acts as the return electrode for stimulation of the SEE or vice versa.

A further aspect of the invention is to provide the aforementioned system wherein the pulse generator is provided with means of wireless control thereby enabling control from outside the body of the pulse generator once implanted.

A further aspect of the invention is to provide the aforementioned system wherein the coupling means comprises at least one electrode lead having a proximal end and a distal end; further wherein the proximal end is electrically connected to the pulse generator; and further wherein the distal end is electrically connected to one or more the electrodes A further aspect of the invention is to provide the aforementioned system wherein the distal end of the electrode lead portion of the effecting electrode is securably positioned in the middle ear of the subject.

A further aspect of the invention is to provide the aforementioned system wherein the pulse generator is implantable in a body of the subject.

A further aspect of the invention is to provide the aforementioned system wherein the pulse generator is implantable in a pharynx of the subject especially the nasopharynx. A further aspect of the invention is to provide the aforementioned system wherein the system additionally comprises a return electrode.

A further aspect of the invention is to provide the aforementioned system wherein the system comprises at least one submucosally implantable electrode.

A further aspect of the invention is to provide the aforementioned system wherein the system comprises at least one subperiostally implantable electrode.

A further aspect of the invention is to provide the aforementioned system wherein the return electrode is positioned in the respective middle ear of the subject.

A further aspect of the invention is to provide the aforementioned system wherein the return electrode is positioned in either pharynx of the subject.

A further aspect of the invention is to provide the aforementioned system wherein the return electrode is positioned in the larynx of the subject.

A further aspect of the invention is to provide the aforementioned system wherein the return electrode is positioned in an oral cavity of the subject.

A further aspect of the invention is to provide the aforementioned system or wherein the return electrode is positioned in a nasal cavity of the subject.

A further aspect of the invention is to provide the aforementioned system wherein the return electrode is positioned in an Eustachian tube of the subject.

A further aspect of the invention is to provide the aforementioned system wherein the system is useful in treating hearing disorders selected from a group consisting of hearing loss, sensoryneural hearing loss, conduction hearing loss, mixed hearing loss, tinnitus, Meniere's disease, and vertigo.

A further aspect of the invention is to disclose a minimally-invasive method for treating a hearing disorder the method comprising steps of;
 a. obtaining an auditory implant system, the system comprising an implantable array of electrodes and a pulse generator, wherein at least one electrode is a cochlear effecting electrode (CEE) adapted for affecting the cochlea of one first ear of a patient, the CEE further adapted for disposing in the associated first Eustachian tube in the proximity of the associated first fenestra rotunda,
 b. implanting the system in the body of a patient, and
 c. operating the system.

A further aspect of the invention is to disclose the aforementioned minimally invasive method comprising steps of obtaining the array further comprising at least one return electrode and obtaining the pulse generator (PG) adapted for generating an effecting electrical signal to the cochlea via the effecting electrode.

A further aspect of the invention is to disclose the aforementioned minimally invasive method comprising further steps of obtaining the system comprising a support structure, in which at least a portion of the array is mounted or is formed therefrom.

A further aspect of the invention is to disclose the aforementioned minimally invasive method wherein the method comprises steps of inserting the support structure with at least a portion of the electrode array through the nosopharyngeal end of the Eustachian tube into the bony portion of the Eustachian tube and adjusting the support structure, thereby achieving a minimally invasive implantation.

A further aspect of the invention is to disclose the aforementioned minimally invasive method comprising steps of obtaining the electrode array further comprising at least one second effecting electrode (SEE) adapted for effecting the associated cochlea of one second ear of a patient, the SEE further adapted for disposition in the associated second Eustachian tube in the proximity of the associated second fenestra rotunda and further wherein the pulse generator is adapted to transmit an electrical signal to the second cochlea via the SEE.

A further aspect of the invention is to disclose the aforementioned minimally invasive method comprising steps of obtaining the system additionally comprising the support structure adapted for
 a. conveying the electrodes from at least a portion of the Eustachian tube to the proximity of the fenestra rotunda, and
 b. anchoring the electrodes from the proximity of the fenestra rotunda to a portion of the Eustachian tube.

A further aspect of the invention is to disclose the aforementioned minimally invasive method comprising steps of obtaining the support structure adapted for transitioning between
 a. a first radially collapsed conveying configuration and
 b. a second radially expanded anchoring configuration, the configurations respectively facilitating the conveyance of the support structure through the portion of Eustachian tube and anchoring of the support structure at the portion of Eustachian tube, thereby disposing at least a portion of the array in proximity of the associated first fenestra rotunda.

A further aspect of the invention is to disclose the aforementioned minimally invasive method comprising additional steps of obtaining an anchoring means attached to or formed from the support structure.

A further aspect of the invention is to disclose the aforementioned minimally invasive method comprising additional steps of obtaining a conveying means protruding from, or formed from the support structure.

A further aspect of the invention is to disclose the aforementioned minimally invasive method comprising additional steps of obtaining the support structure comprising a. a generally tubular engagement portion adapted to fit longitudinally in the Eustachian tube, the tubular engagement portion further comprising a proximal end, a distal end and a body connecting therebetween;

b. at least one the effecting electrode disposed near the distal end of the engagement portion, the effecting electrode comprising a proximal insulated lead portion and a distal conductive tip portion, further wherein the distal end of engagement portion is adapted to internally engage a portion of the Eustachian tube such that the distal conductive tip portion of the effecting electrodes are anchored in position when disposed in the proximity to the fenestra.

A further aspect of the invention is to disclose the aforementioned minimally invasive method comprising additional steps of obtaining a delivery apparatus for releasably deploying the support structure within the Eustachian tube thereby actuating transitioning of the engagement portion from the first radially collapsed configuration to the second radially expanded configuration.

A further aspect of the invention is to disclose the aforementioned minimally invasive method comprising additional steps of obtaining the delivery apparatus further comprising an endoscopic visualization channel.

A further aspect of the invention is to disclose the aforementioned minimally invasive method. The method comprises steps of obtaining the endoscopic visualization channel has an external diameter between about 400 micrometers to about 1000 micrometers.

A further aspect of the invention is to disclose the aforementioned minimally invasive method comprising additional steps of obtaining the support structure adapted for endoluminal retrieval following the transition from the radially expanded configuration to the radially collapsed configuration.

A further aspect of the invention is to disclose the aforementioned minimally invasive method comprising additional steps of obtaining the support structure provided with a plurality of proximally disposed retrieval handles, the handles adapted to engage with and actuate a retrieval apparatus, the retrieval apparatus provided with means of transitioning the support structure from the radially expanded configuration to radially collapsed configuration and subsequent disposition into a tubular sheath.

A further aspect of the invention is to disclose the aforementioned minimally invasive method comprising additional steps of obtaining the engagement portion comprising a self expanding stent-like structure.

A further aspect of the invention is to disclose the aforementioned minimally invasive method comprising additional steps of obtaining the engagement portion comprising an open weave construction of helically wound filaments of a superelastic alloy.

A further aspect of the invention is to disclose the aforementioned minimally invasive method comprising additional steps of obtaining the generally tubular engagement portion of length between about 4 millimeters to about 14 millimeters.

A further aspect of the invention is to disclose the aforementioned minimally invasive method comprising additional steps of obtaining the generally tubular engagement portion of cross section between about 4 millimeters to about 14 millimeters.

A further aspect of the invention is to disclose the aforementioned minimally invasive method comprising additional steps of obtaining the generally tubular engagement portion wherein the cross section of the engagement portion is conic, expanding from the proximal end towards the distal end of the tubular engagement portion.

A further aspect of the invention is to disclose the aforementioned minimally invasive method comprising additional steps of obtaining the generally tubular engagement portion wherein the distal end of the engagement portion is characterized by an oval cross section of about 2 millimeters×about 5 millimeters.

A further aspect of the invention is to disclose the aforementioned minimally invasive method wherein the method further comprises additional steps of a. obtaining the support structure provided with an extension arm adapted for post implant adjustment by the physician b. adjusting post implant the extension arm with or without a special tool for the purpose so as to facilitate final fitting of the auditory implant system in place.

A further aspect of the invention is to disclose the aforementioned minimally invasive method comprising additional steps of providing the pulse generator with coupling means to any of the electrodes.

A further aspect of the invention is to disclose the aforementioned minimally invasive method comprising additional steps of selecting the coupling means from a group consisting of a radio frequency link, an acoustic energy link, a magnetic induction link or an electric lead.

A further aspect of the invention is to disclose the aforementioned minimally invasive method comprising additional steps of obtaining the pulse generator provided with means of remote control from outside the body.

A further aspect of the invention is to disclose the aforementioned minimally invasive method comprising additional steps of providing the coupling means further comprising at least one electrode lead having a proximal end and a distal end; electrically connecting the proximal end to the pulse generator; and electrically connecting the distal end to one or more the electrodes.

A further aspect of the invention is to disclose the aforementioned minimally invasive method comprising additional steps of securely positioning the distal end of the electrode lead portion of the effecting electrode in the middle ear of the subject.

A further aspect of the invention is to disclose the aforementioned minimally invasive method comprising additional steps of implanting the pulse generator in a body of the subject.

A further aspect of the invention is to disclose the aforementioned minimally invasive method comprising additional steps of implanting the pulse generator in a pharynx of the subject especially the nasopharynx.

A further aspect of the invention is to disclose the aforementioned minimally invasive method comprising additional steps of obtaining the system additionally comprising a return electrode.

A further aspect of the invention is to disclose the aforementioned minimally invasive method comprising additional steps of implanting at least one electrode submucosally. A further aspect of the invention is to disclose the aforementioned minimally invasive method comprising additional steps of implanting at least one the electrode subperiostally.

A further aspect of the invention is to disclose the aforementioned minimally invasive method comprising additional steps of positioning the return electrode in the respective middle ear of the subject.

A further aspect of the invention is to disclose the aforementioned minimally invasive method comprising additional steps of positioning the return electrode in either pharynx of the subject.

A further aspect of the invention is to disclose the aforementioned minimally invasive method comprising additional steps of positioning the return electrode in the larynx of the subject.

A further aspect of the invention is to disclose the aforementioned minimally invasive method comprising additional steps of positioning the return electrode in an oral cavity of the subject.

A further aspect of the invention is to disclose the aforementioned minimally invasive method comprising additional steps of positioning the return electrode in a nasal cavity of the subject.

A further aspect of the invention is to disclose the aforementioned minimally invasive method comprising additional steps of positioning the return electrode in a Eustachian tube of the subject.

A further aspect of the invention is to disclose the aforementioned minimally invasive method comprising additional steps of obtaining the system useful in treating hearing disorders, and selecting the disorder to be treated from a group consisting of hearing loss, sensoryneural hearing loss, conduction hearing loss, mixed hearing loss, tinnitus, Meniere's disease and vertigo.

DETAILED DESCRIPTION OF THE DRAWINGS

Figure 1:
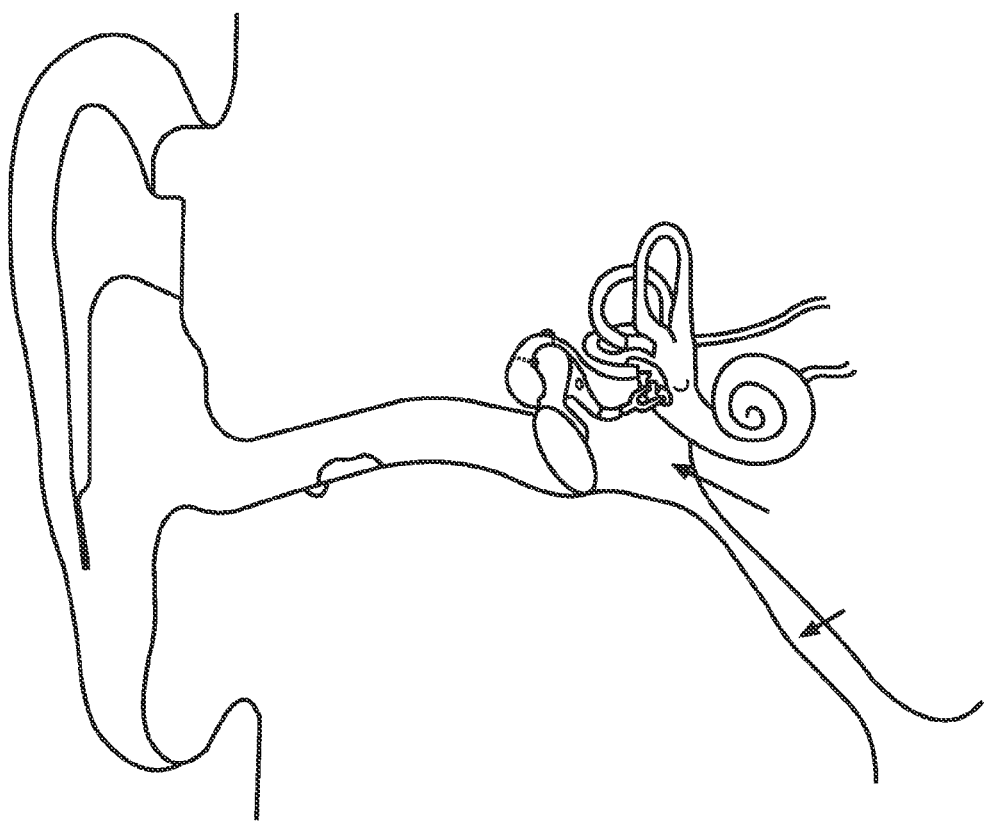
FIG. 1 schematically illustrates a preferred embodiment of an aspect of the invention.

In the following description, various aspects of the invention will be described. For the purposes of explanation, specific configurations and details are set forth in order to provide a thorough understanding of the invention. However, it will be also apparent to one skilled in the art that the invention may be practiced without specific details presented herein. Furthermore, well-known features may be omitted or simplified in order not to obscure the invention.

It is well known that sub-threshold stimulation—either excitatory or inhibitory—can be effective in treating various brain disorders via epidural, or dural electrodes or "deep brain stimulation" electrodes. An interesting aspect of sub-threshold nerve stimulation is that by itself (and per its definition), it is sub-sensory. Namely one cannot directly sense the effect of subthreshold nerve stimulation.

Specifically, excitatory subthreshold stimulation in fact acts as a neural "amplifier" by increasing the probability of a nerve impulse to occur, or looking at it through a different point of view—reduces the amount of input stimuli required for a neuron to fire an impulse. Inhibitory subthreshold stimulation works exactly the other way around. Namely, in effect it acts as an "attenuator" of nerve activity. In fact, such an inhibitory signal increases the amount of stimuli necessary to elicit an impulse over the axon. It is therefore likely to expect that applying subthreshold stimulation—either excitatory or inhibitory—in a non specific manner to the cochlear nerve, could have a significant effect on various hearing disorders, assuming the cochlea still maintains some sensory function. Even if the hearing loss has a conductive component, excitatory subthreshold stimulation could compensate for some of the lost hearing sensitivity. As tinnitus is not considered a disease, but rather a symptom that could result from different causes (e.g. tinnitus is often linked to hearing loss)—it is also likely to expect that subthreshold excitatory stimulation could provide some relief from tinnitus.

The middle ear is a bony cavity, but it contains a few "windows". One of these "windows" allows, for example, the tympanic membrane to create a relatively effective acoustic coupling between the external ear and the bony conductive chain of the middle ear. Additional "windows" exist also between the middle ear and the inner ear, and the two of those are the fenestra vestibuli (also called the "oval window"—fenestra ovalis) and the fenestra cochleae (also called the "round window", fenestra rotunda). The latter two windows in the bony cavity of the middle ear, allows direct membranous communication between the air-filled cavity of the middle ear and the vestibular and cochlear organs (they are actually two portions of one anatomical entity) of the inner ear, respectively.

The fenestra cochlea (fenestra rotunda) is situated below and a little behind the fenestra vestibuli, from which it is separated by a rounded elevation, the promontory. It is placed at the bottom of a funnel-shaped depression and, in the macerated bone, leads into the cochlea of the internal ear; in the fresh state it is closed by a membrane, the secondary tympanic membrane, which is concave toward the tympanic cavity, convex toward the cochlea. This membrane consists of three layers: an external, or mucous, derived from the mucous lining of the tympanic cavity; an internal, from the lining membrane of the cochlea; and an intermediate, or fibrous layer.

Most body membranes (excluding the skin), especially the mucous ones, are relatively conductive to electrical current, due to their relatively high electrolyte concentrations. Therefore, it is likely to expect that an electrode that is placed in the middle ear, physically adjacent to such a membrane, will be effective in driving electrical current into the cochlea.

In the adult, the Eustachian tube can be visualized as two truncated cones attached at their narrowed ends. It runs from the middle ear to the nasopharynx and is approximately 31-38 mm in length. Its lumen is roughly triangular and has average diameter of 2-3 mm. The lumen is lined by ciliated psuedostratified, columnar epithelium, which sweeps material from the middle ear to the nasopharynx.

Mucous glands predominate near the pharyngeal orifice, and there is a gradual change to a mixture of goblet, columnar, and ciliated cells as the middle ear is approached. The Eustachian tube is composed of an osseous and a cartilaginous portion. The osseous Eustachian tube or protympanum measures 11 to 14 mm and extends from the anterior and medial portion of the petrous temporal bone. Its orifice is oval shaped, measures 5×2 mm and is located above the floor of the middle ear space. The cartilaginous portion measures 20-25 mm and opens into the nasopharynx approximately 10 mm above the plane of the hard palate. The cartilage protrudes into the nasopharynx, and the protruding portion is known as the torus tubarius. The fossa of Rosenmuller is this area in the nasopharynx superior to the torus tubaris.

The cartilaginous portion is composed of one main piece of cartilage and can be accompanied by several accessory cartilages. Its composition and elasticity is similar to that found in the pinna and nose. It is attached at the sphenoid sulcus on the base of skull superiorly and its anteriomedial end is attached to a small tubercle on the posterior edge of the medial pterygoid plate. The Eustachian tube evidently represents a much less invasive implantation route, compared to contemporary methods for placing cochlear electrodes directly in the middle ear—risking infection and possibly irreversibly damage to sensitive sensory and other neural structures.

Reference is now made to the following figures which describe and illustrate various aspects of the invention. For the purposes of explanation, specific configurations and details are set forth in order to provide a thorough understanding of the invention. However, it will be also apparent to one skilled in the art that the invention may be practiced without specific details presented herein. Furthermore, well-known features may be omitted or simplified in order not to obscure the invention.

The term "electrode" hereinafter refers to an active element that couples the electric current to target tissues. The terms "effecting electrode" or "effecter electrode" refers to an electrode that delivers an activating electrical signal to the target tissue. The activating electric signal is an electrical waveform, and, in a preferred embodiment of the invention, is an inhibitory signal. In other embodiments of the invention the delivered electrical waveform has a stimulating effect, and in other embodiments, the delivered waveform has an inhibitory effect. Hence, the term effecting or effect electrodes may sometimes refer herein to stimulating electrodes and sometimes to inhibiting electrodes. Both types are envisaged in embodiments of the invention.

The term "structural support" hereinafter refers to an element of the invention which is optionally adapted to assume more than one configuration to enable it to fit the Eustachian canal. This may be done by self expanding. The structural support has further attributes, and these comprise the following: At least one effecting electrode is formed from the aforementioned support or is attached to it. At least one return electrode is formed from the aforementioned support or is attached to it. The structural support itself is able to anchor within the Eustachian canal. In other embodiments of the invention the structural support has an anchoring element attached to it and/or arising from it. In some embodiments of the invention the system comprises a support structure provided with an extension arm. The extension arm is adapted for post implant adjustment by the physician with or without a special tool for the purpose.

It is acknowledged herein that, in some embodiments of the invention, the structural support, anchoring element or the extension arm may be fitted finally or adjusted finally by the physician, by bending twisting, deforming or altering the structural support, directly or by means of a special tool for the purpose.

In some embodiments of the invention portions of the structural support, anchoring element or the extension arm may be made of super elastic materials, shape memory materials or stainless steel, suitable for implanting in a human. The structural support itself is able to convey the electrodes within the Eustachian canal. In other embodiments of the invention the structural support is conveyed by a conveying element within the Eustachian tube.

Figure 2:
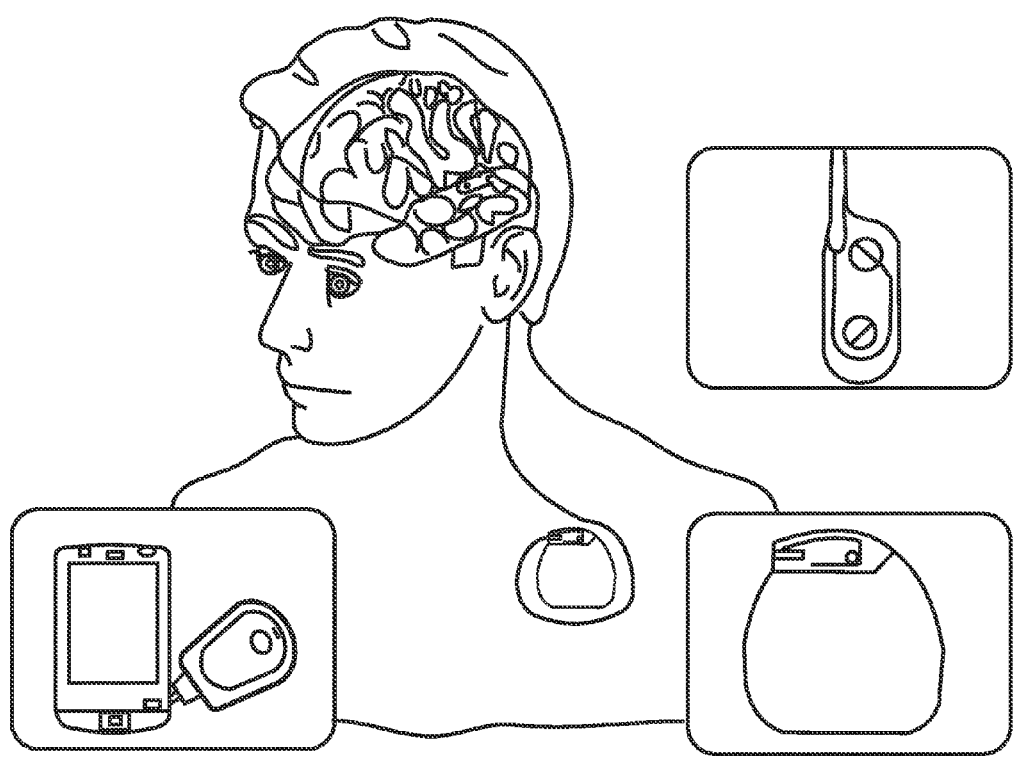
FIG. 2 schematically illustrates a preferred embodiment of an aspect of the invention.

Reference is made to FIG. 1, which is a schematic illustration of the anatomy of the ear. Reference is made to the schematic representation FIG. 2 of prior art cortical implants. It can be seen from the figure that this technique known to prior art is highly invasive, necessitating implantation of electrodes into the brain.

Figure 3:
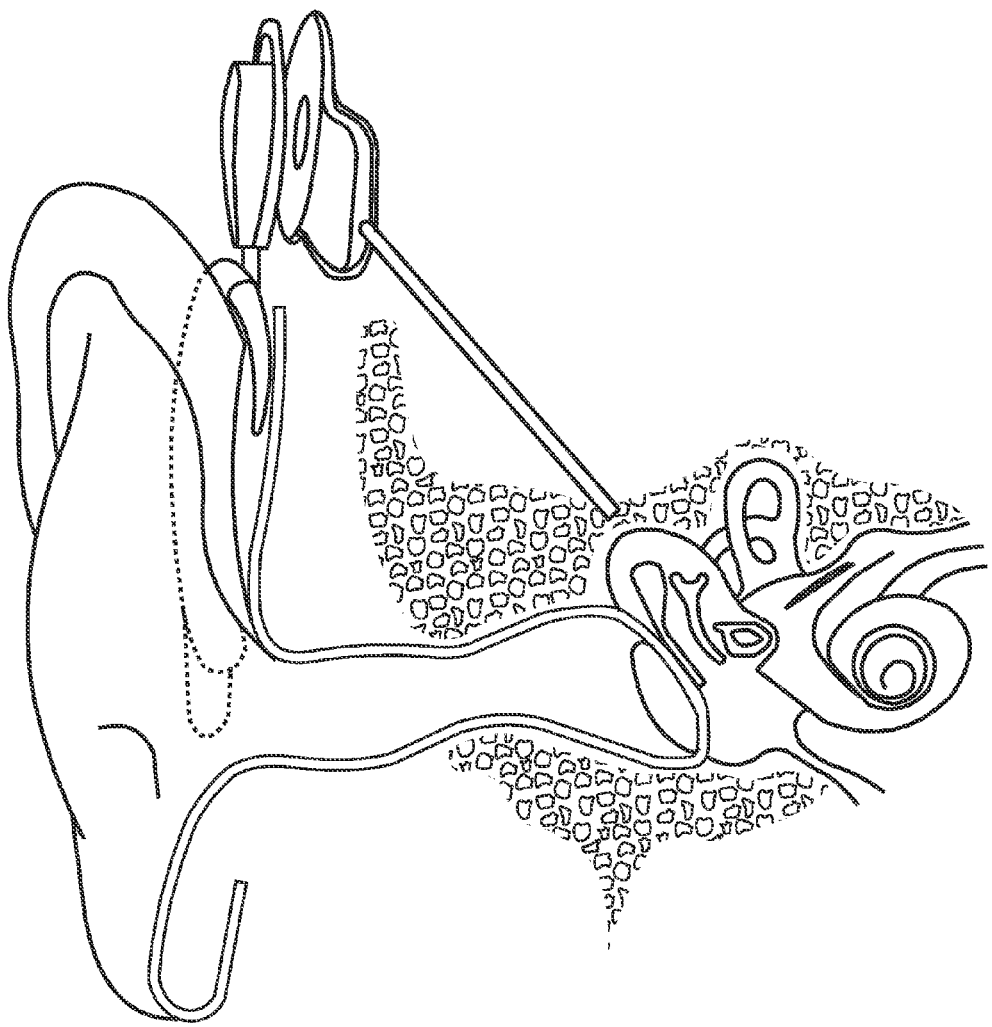
FIG. 3 schematically illustrates a preferred embodiment of an aspect of the invention.

Reference is now made to the schematic representation FIG. 3 of prior art cochleal implants. It can be seen that here too, the prior art technique is invasive, necessitating direct implantation.

BEST MODE OF THE PRESENT INVENTION

Figure 4:
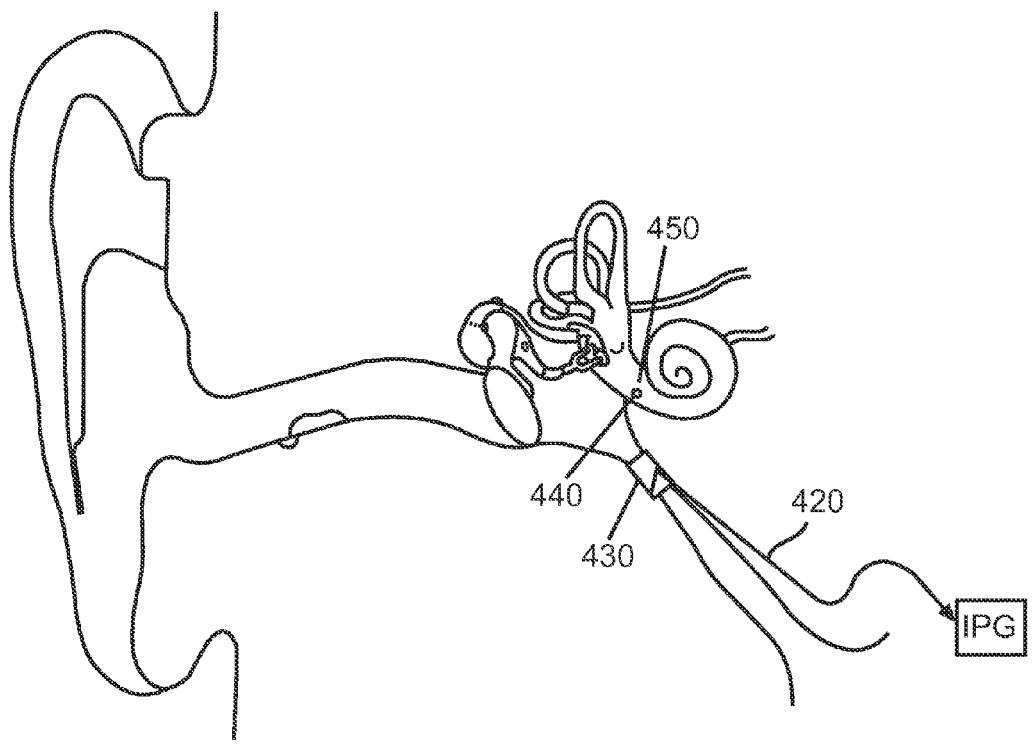
FIG. 4 schematically illustrates a preferred embodiment of an aspect of the invention.

The core aspect of the present invention is schematically illustrated in FIG. 4 showing a best mode of the invention: An electrical stimulator or Implantable Pulse Generator (IPG)—that is implanted below the mucosal lining of the nasopharynx (nasal part of the pharynx) 420 is the Middle Ear Stimulation Lead—This is an electrode lead connected to the IPG and is used to deliver inhibition or stimulation to the cochlear nerve via electrical contact in the middle ear. Note that the lead 420 travels along the interior of the Eustachian tube and is minimally invasive compared to the aforementioned prior art. The adaptor or support structure 430 is located and anchored in the Eustachian tube after having been radially expanded to fit therein. The electrode 440 is placed adjacent to the cochlear window 450, which is the protective membrane that interfaces with the perilymph fluid of the middle ear.

Figure 5:
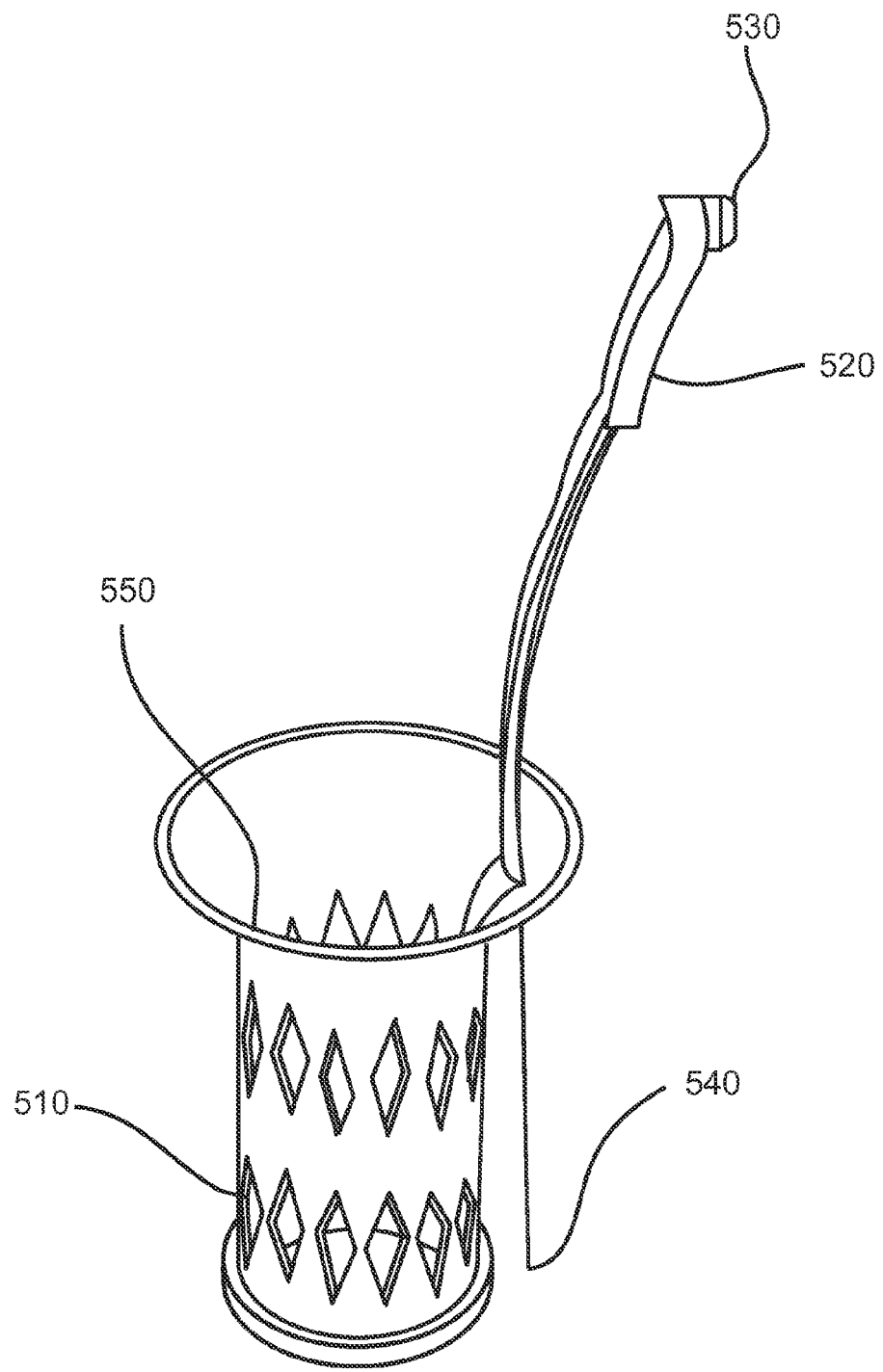
FIG. 5 schematically illustrates a preferred embodiment of an aspect of the invention, FIG. 6 schematically illustrates a preferred embodiment of an aspect of the invention.

Another exemplary embodiment of the invention is schematically represented in FIG. 5. The support structure 510 is also an adaptor comprising an isolation cap 520 effecter electrode 530, lead to IPG 540, anchoring means 550, which in this case is an expanded stent-like part of the structure.

Figure 6:
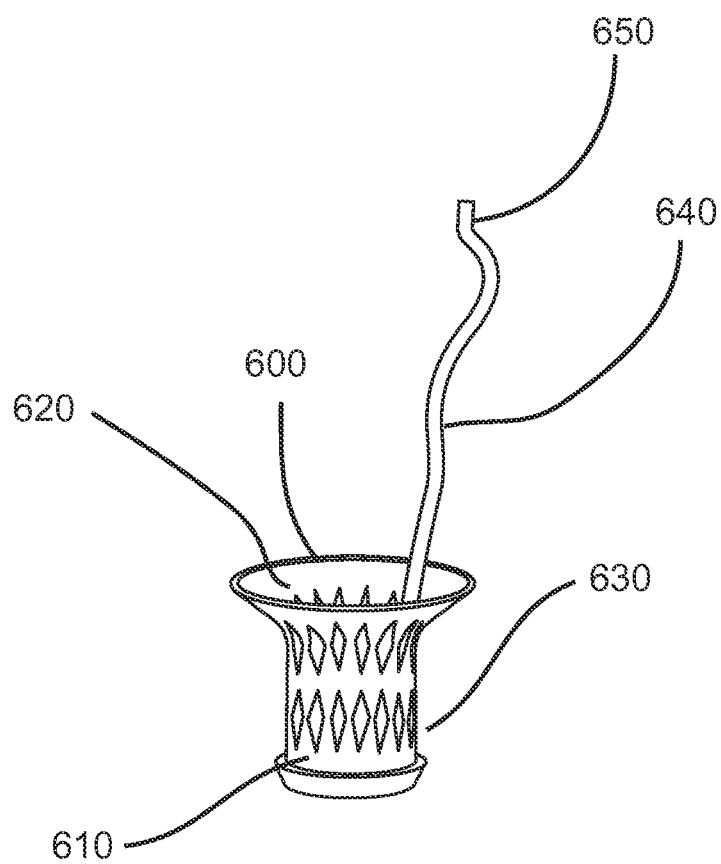

FIG. 6 schematically illustrates a preferred embodiment of an aspect of the invention. The exemplary adaptor is shown in its expanded configuration. The aforementioned adaptor comprises a generally tubular engagement portion 600 adapted to fit longitudinally in the Eustachian tube. The tubular engagement portion further comprises a proximal end 610, a distal end 620 and a body 630 connecting there between. At least one projecting member 640 is attached to the body and is disposed near the distal end of the engagement portion. The projecting member comprises the effecting electrode, which comprises a proximal insulated lead portion, and a distal conductive tip portion 650. It is a core feature of the present invention that the distal end 620 of the engagement portion 600 is adapted to internally engage a portion of the Eustachian tube (not shown) such that the distal conductive tip portion 650 of the effecting electrodes are anchored in position when disposed in the proximity to the fenestra rotunda.

In some aspects of the invention, the configurations of the effecting electrode comprise a wire electrode coiled around the stapes, an open cuff electrode positioned around the stapes, a wire electrode coiled around the incus, depicts a coiled wire electrode occupying an infero-medial portion of the middle-ear, a flat "disc"-shaped electrode positioned around the medial end of the staples, or a circular wire electrode barb-anchored around the secondary tympanic membrane.

Figure 7:
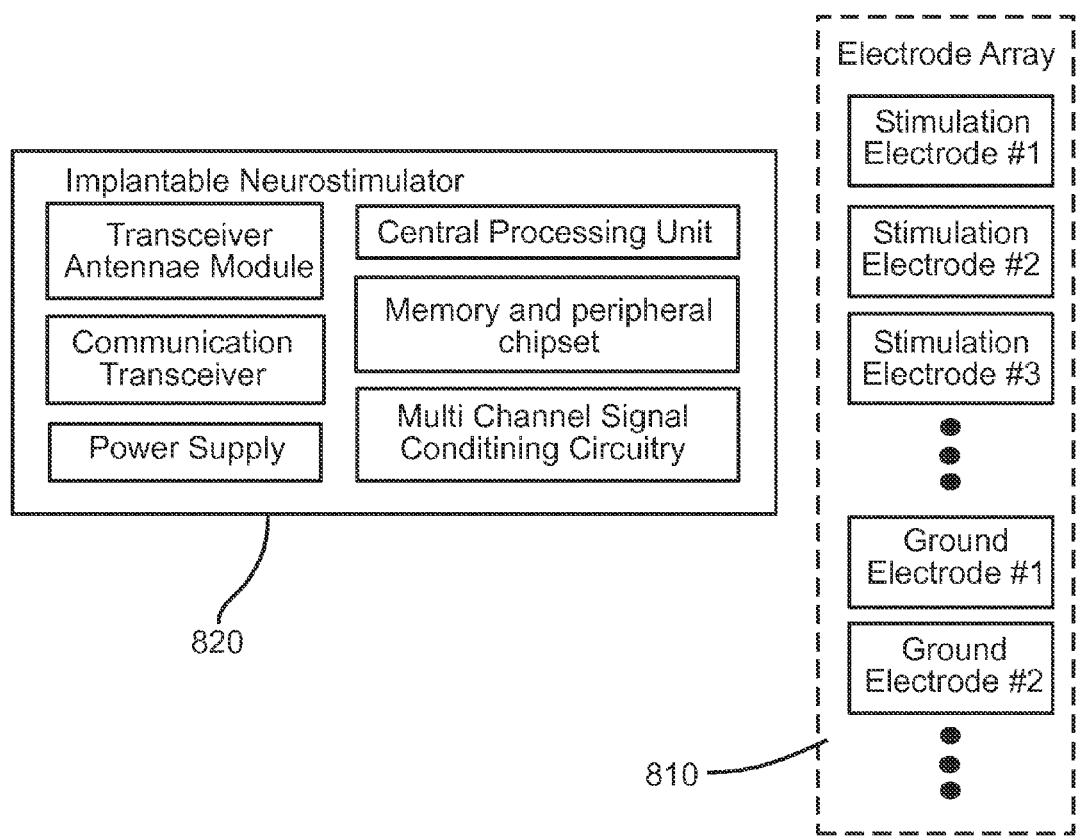
FIG. 7 schematically illustrates a preferred embodiment of an aspect of the invention.

FIG. 7 depicts a simplified block diagram of an implantable pulse generator (IPG), connected with an electrode array according to aspects of the invention. The pulse generator includes a communication module 820. In other selected embodiments, the IPG may comprise of an energy conversion member for external energizing. In yet other selected embodiments, the IPG may further comprise an energy storage unit, that is adapted to store the energy that is wirelessly transmitted from a loci outside the subject's body. Reference is now made to the block representing the electrode array 810. The array comprising at least 1 effecting electrode (three in this case) and at least one return electrode (two in this case). The return electrode hereinafter has the opposite polarity to the effecting electrode. Reference is now made to the block representing the Implantable Neurostimulator 820 which optionally contains components selected from a group consisting of Central Processing Unit, Memory and peripheral chipset, Multi Channel Signal Conditioning Circuitry, and Power Supply. This block supplies the electrical signals, as an electrical waveform, to the electrode array, which delivers the signals to the cochlea. In some embodiments of the invention—a handheld computer is attached to a programming device that allows communication with the implanted IPG device. This system allows the clinician to change electrical waveform parameters (inhibitory or stimulatory) and to turn the device on and off.

Figures 8A, 8B, 8C:
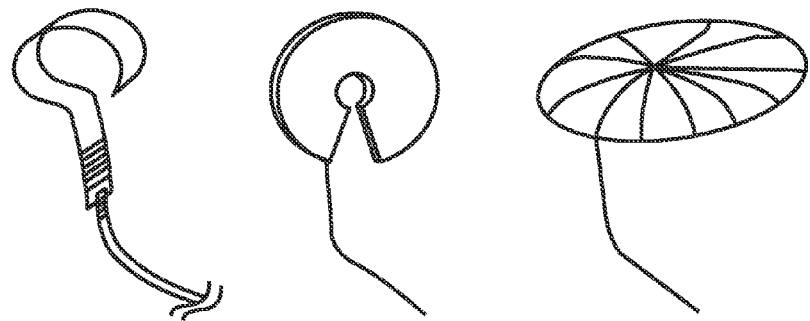
FIG. 8 schematically illustrates a preferred embodiment of an aspect of the invention.
Figures 8D, 8E:
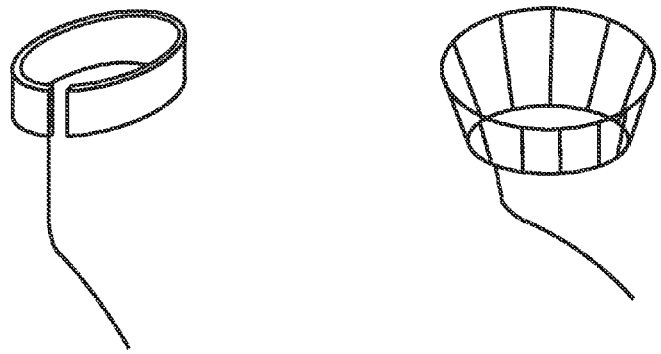

Reference is now made to FIG. 8 which schematically illustrates various possible configurations for the effecting electrode and/or the return electrode. FIG. 8*a-c* depicts three different sample configurations for an effecter electrode (inhibiting or stimulating) that is adapted for introduction into the middle ear via the Eustachian tube. FIG. 8*d-e* depicts two different sample configurations for a return electrode or that is to be positioned inside (along) the Eustachian tube.

Figures 9A, 9B, 9C:
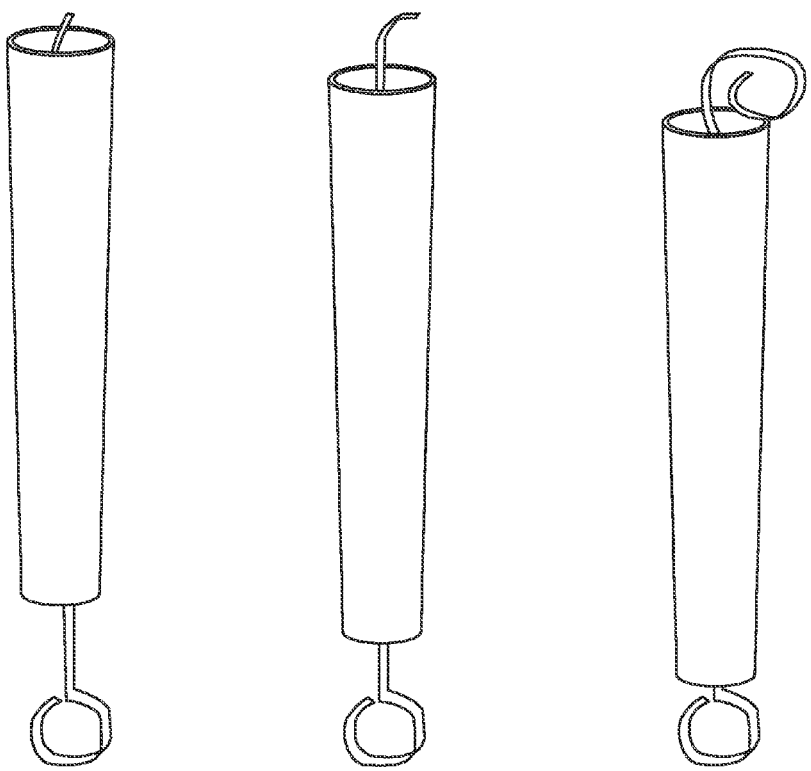
FIG. 9 schematically illustrates a preferred embodiment of an aspect of the invention.

FIG. 9 schematically depicts 3 stages of deployment (a-c) of a self-coiling electrode connected to its corresponding electrode (wire) lead, that is adapted for insertion via the Eustachian tube (auditory tube) and through manual manipulation of its proximal end—positioning of the self-coiling wire electrode around, or within a selected structure in the middle ear.

Figure 10:
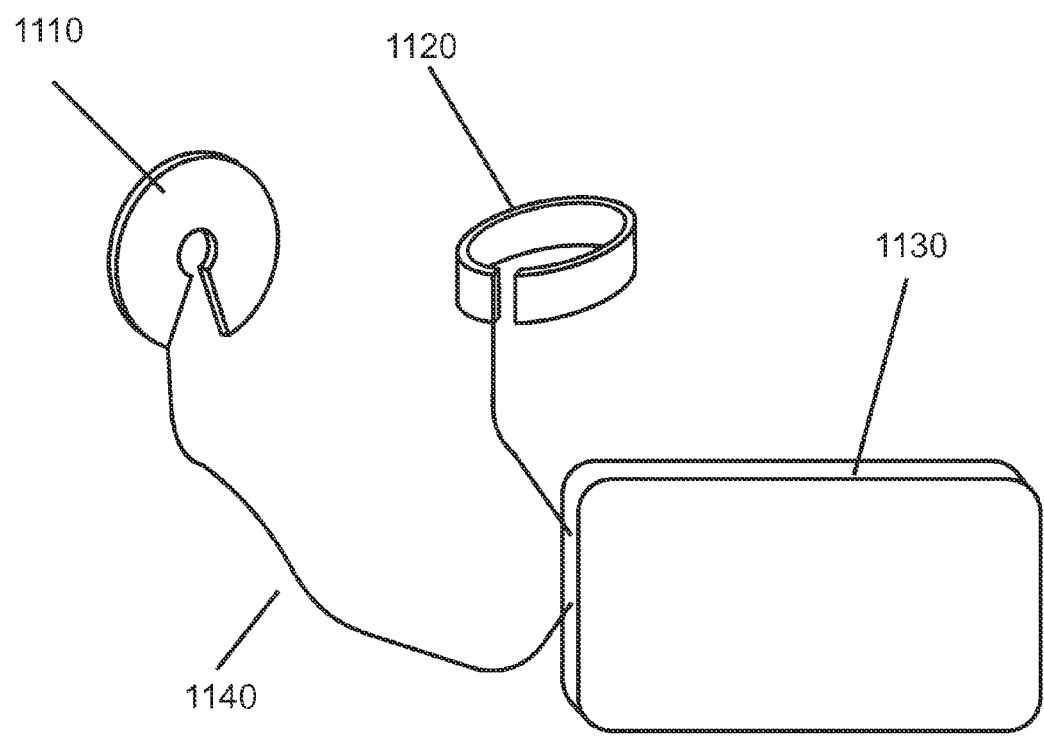
FIG. 10 schematically illustrates a preferred embodiment of an aspect of the invention.

Reference is now made to FIG. 10 schematically depicting a preferred embodiment of the current invention. The preferred embodiment comprises 1 effecter electrode 1110 for placement in the middle ear via the Eustachian tube, 1 return electrode 1120 that is adapted to be located in an Eustachian tube (optionally contralaterally to its corresponding return electrode) and an implantable pulse generator 1130 (IPG) that connects to the two aforementioned electrodes via lead wires 1140,1150.

Figure 11:
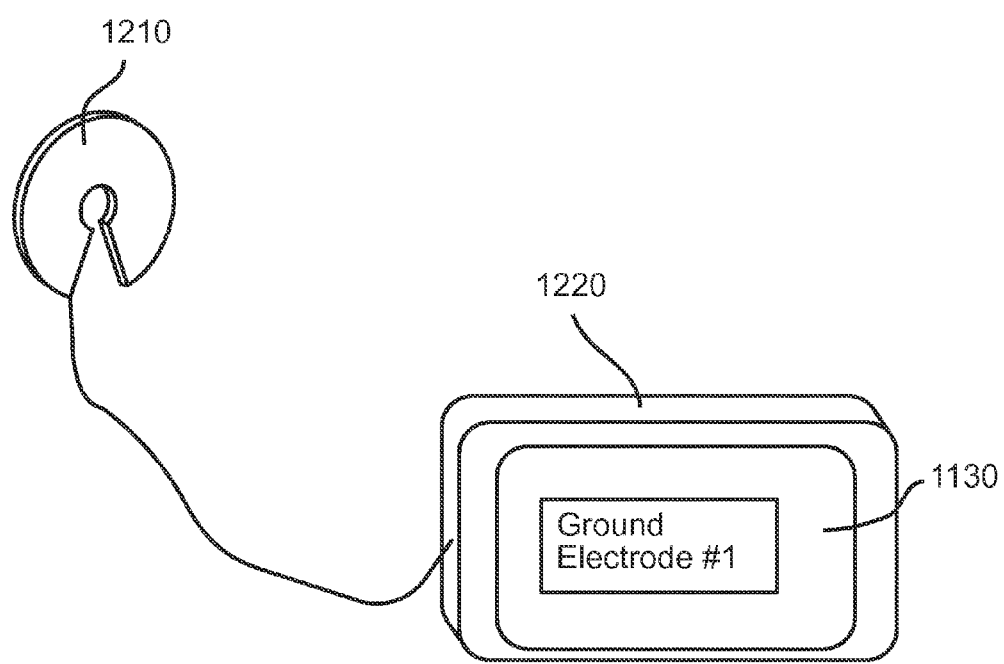
FIG. 11 schematically illustrates a preferred embodiment of an aspect of the invention.

FIG. 11 schematically depicts an exemplary embodiment of the invention wherein the return electrode 1220 is positioned upon the chassis 1230 of the IPG. The effecter electrode is shown as 1210.

Figure 12:
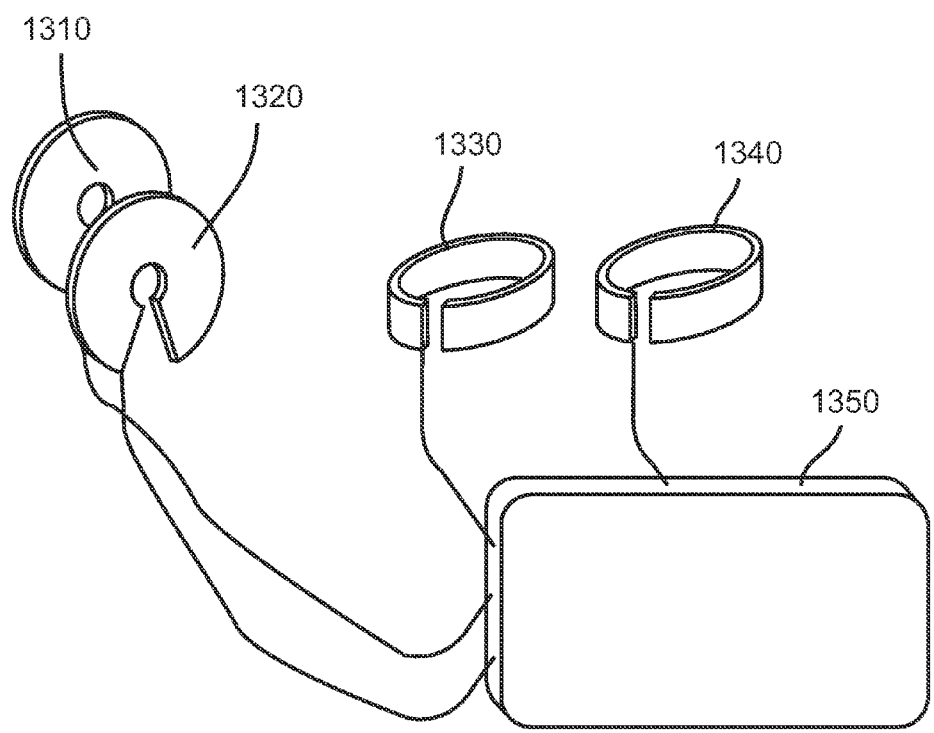
FIG. 12 schematically illustrates a preferred embodiment of an aspect of the invention.

Reference is now made to FIG. 12 schematically depicting an exemplary dual channel embodiment of the current invention, comprising 2 effecter electrodes 1310, 1320 for placement in the middle ear via the Eustachian tube and 2 return electrodes 1330, 1340 that are adapted to be located in an Eustachian tube (possibly—contralaterally to its corresponding stimulation electrode) and an implantable pulse generator 1350 (IPG) that connects to the four aforementioned electrodes via lead wires.

While a number of exemplary aspects and embodiments have been discussed above, those of skill in the art will recognize certain modifications, permutations, additions and sub-combinations thereof. It is therefore intended that the following appended claims hereafter introduced be interpreted to include all such modifications, permutations, additions and sub-combinations as are within their true spirit and scope.

The invention claimed is:

1. A minimally-invasive auditory implant system for treating a hearing disorder, said system comprising:
   i) an implantable array of electrodes;
   ii) a pulse generator (PG);
   iii) a support structure in which at least a portion of said array is mounted;
   wherein at least one electrode in said array is a cochlear effecting electrode (CEE) adapted for affecting a cochlea of one first ear of a patient, said CEE further adapted for disposition in an associated first Eustachian tube in the proximity of an associated first fenestra rotunda; wherein
   said support structure is adapted for transitioning between a radially collapsed, conveying configuration and a radially expanded, anchoring configuration, said configurations respectively facilitating conveying said support structure through said associated first Eustachian tube and anchoring said support structure at said associated first Eustachian tube, enabling disposing at least a portion of said array in proximity of said associated fenestra rotunda; wherein
   said support structure comprises a generally tubular engagement portion adapted to fit longitudinally in said Eustachian tube, comprising a proximal end, a distal end and a body connecting therebetween, said engagement portion having a length between about 4 millimeters to about 14 millimeters and a cross section between about 4 square millimeters to about 14 square millimeters; wherein
   said CEE is disposed near said distal end of said engagement portion, and wherein said distal end is adapted to internally engage a portion of said Eustachian tube such that said CEE is anchored in said proximity to said fenestra; and wherein
   said system additionally comprises a delivery apparatus for releasably deploying said support structure within said Eustachian tube thereby actuating transitioning of said engagement portion from said radially collapsed, conveying configuration to said radially expanded, anchoring configuration.

2. A system according to claim 1 wherein said electrode array further comprises at least one second effecting electrode (SEE) adapted for affecting an associated cochlea of one second ear of said patient, said SEE further adapted for disposition in an associated second Eustachian tube in the proximity of an associated second fenestra rotunda and further wherein said pulse generator is adapted to deliver an electrical signal to said second cochlea via said SEE.

3. A system according to claim 1 wherein said delivery apparatus comprises an endoscopic visualization channel.

4. A system according to claim 1, wherein said pulse generator is adapted for generating an electrical signal to said cochlea via said CEE, and provided with coupling means to said CEE, said coupling means being selected from the group consisting of a radio frequency link, an acoustic energy link, a magnetic induction link, and an electric lead, said pulse generator being implanted in the body of said patient and provided with means of wireless control thereby enabling its control from outside the body.

5. A system according to claim 1 wherein said support structure comprises a return electrode positioned in a body site of said patient selected from the group consisting of middle ear, pharynx, larynx, oral cavity, nasal cavity, and Eustachian tube.

6. A system according to claim 1 wherein said system comprises at least one submucosally or subperiostally implantable electrode.

7. A system according to claim 1 wherein said hearing disorder is selected from the group consisting of hearing loss, sensoryneural hearing loss, conduction hearing loss, mixed hearing loss, tinnitus, Meniere's disease, and vertigo.

8. A minimally-invasive method for treating a hearing disorder said method comprising the steps of
   i) obtaining the auditory implant system of claim 1;
   ii) conveying said support structure through the Eustachean tube and anchoring it in said Eustachean tube, thereby disposing said CEE in the proximity of said fenestra rotunda;
   iii) generating in said PG an electrical signal and transmitting said signal to said cochlea via said CEE; wherein said step ii comprises releasably deploying said support structure within said Eustachian tube, thereby actuating transitioning of said engagement portion from said radially collapsed, conveying configuration to said radially expanded, anchoring configuration; adjusting, after implantation, said support structure provided with an extension arm and adapted for post implant adjustment by a physician, so as to fitting said auditory implant system in place; and
   positioning said CEE in said middle ear of said patient.

9. A method according to claim 8 wherein said method comprises steps of inserting said support structure with at least a portion of said electrode array through the nosopharyngeal end of said Eustachian tube into the bony portion of said Eustachian tube and adjusting said support structure, thereby achieving a minimally invasive implantation.

10. A method according to claim 8 comprising a step of obtaining at least one second effecting electrode for affecting an associated cochlea of a second ear of said patient, and disposing said second effecting electrode in the proximity of an associated second fenestra rotunda, wherein said pulse generator is adapted to transmit an electrical signal to said second cochlea via said second effecting electrode.

11. A method according to claim 8 further comprising the step of delivering an endoscopic visualization channel.

12. A method according to claim 8 further comprising at least one additional step selected from
   i) implanting said pulse generator in the body of said patient;
   ii) implanting said pulse generator in pharynx of said patient;
   iii) implanting said pulse generator in nasopharynx of said patient;
   iv) implanting at least one electrode submucosally; and
   v) implanting at least one electrode subperiostally.

13. A method according to claim 8 further comprising positioning a return electrode in a body site of said patient selected from a middle ear, pharynx, larynx, oral cavity, nasal cavity, and Eustachian tube.

14. A method according to claim 8 wherein said disorder is selected from the group consisting of hearing loss, sensoryneural hearing loss, conduction hearing loss, mixed hearing loss, tinnitus, Meniere's disease, and vertigo.

* * * * *